(12) United States Patent
Vetter et al.

(10) Patent No.: US 6,296,625 B1
(45) Date of Patent: Oct. 2, 2001

(54) FINGER BRACE FOR HYPODERMIC SYRINGE

(75) Inventors: Udo J. Vetter, Ravensburg; Thomas Otto, Weingarten; Joachim Glocker, Weingargen, all of (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 0 days.

(21) Appl. No.: 09/602,708

(22) Filed: Jun. 26, 2000

(30) Foreign Application Priority Data

Jun. 26, 1999 (DE) .............................................. 199 29 325

(51) Int. Cl.⁷ .................................................. A61M 5/315
(52) U.S. Cl. .............................................................. 604/227
(58) Field of Search ..................................... 604/227, 187, 604/218, 232, 220, 221

(56) References Cited

U.S. PATENT DOCUMENTS

| | | |
|---|---|---|
| 5,320,603 | 6/1994 | Vetter . |
| 5,338,309 * | 8/1994 | Imbert ................................... 604/187 |
| 5,419,775 * | 5/1995 | Haffner et al. ........................ 604/227 |
| 5,897,532 * | 4/1999 | Spallek et al. .................... 604/227 X |

FOREIGN PATENT DOCUMENTS 197 23 851    8/1998 (DE) .

* cited by examiner

*Primary Examiner*—Manuel Mendez
(74) *Attorney, Agent, or Firm*—Herbert Dubno; Andrew Wilford

(57) ABSTRACT

A syringe assembly has a tubular syringe body centered on and extending along an axis and formed at a rear end with a radially outwardly projecting rim. A finger brace of limitedly elastically deformable material is formed with an end plate bearing axially forward on the rear end and formed with a central hole. A tube projects axially forward from the hole of the plate into the body at the rear syringe end, and a collar extends axially forward form the plate outside the tube and is formed with a plurality of angularly spaced and radially inwardly projecting teeth engaged under the rim. The plate is also formed adjacent each of the teeth with an axially throughgoing and angularly elongated slot defining a radially elastically deflectable side portion carrying the respective tooth.

9 Claims, 5 Drawing Sheets

FINGER BRACE FOR HYPODERMIC SYRINGE

FIELD OF THE INVENTION

The present invention relates to a hypodermic syringe. More particularly this invention concerns a subassembly comprising a finger brace and syringe body.

BACKGROUND OF THE INVENTION

A standard hypodermic syringe as described in commonly owned U.S. Pat. No. 5,320,603 has a cylindrically tubular body having a front end closed by a plug formed with a central passage extending along the axis of the body and a rear end provided with a piston longitudinally axially displaceable in the body. The read end carries a transversely projecting finger brace. A quantity of liquid to be injected is held in the body between the piston and the plug and a needle is fitted to the passage at its front end so that forward displacement of the piston by a plunger forces the liquid out of the body through the needle. The syringe is typically held with two of the user's fingers engaged on opposite sides of the rear end of the syringe with forward-facing surfaces of the brace and the user's thumb bearing on the rear end of the plunger.

OBJECTS OF THE INVENTION

It is therefore an object of the present invention to provide an improved hypodermic syringe Another object is the provision of such an improved hypodermic syringe which overcomes the above-given disadvantages, that is which has an improved finger brace that is particularly constructed to act as a stop limiting the stroke of the plunger.

SUMMARY OF THE INVENTION

A syringe assembly has a tubular syringe body centered on and extending along an axis and formed at a read end with a radially outwardly projecting rim. A finger brace of limitedly elastically deformable material is formed with an end plate bearing axially forward on the rear end and formed with a central hole. A tube projects axially forward from the hole of the plate into the body at the rear syringe end, and a collar extends axially forward from the plate outside the tube and is formed with a plurality of angularly spaced and radially inwardly projecting teeth engaged under the rim. The plate is also formed adjacent each of the teeth with an axially throughgoing and angularly elongated slot defining a radially elastically deflectable side portion carrying the respective tooth.

Thus such a finger brace can be snapped in place over the rear end of the syringe body and will remain solidly locked to the body. The tube extending down into the syringe body serves as a stop limiting rearward travel of a piston carried on a plunger extending axially through the hole in the plate. The length of the tube can be varied to set different strokes for the piston so that, for instance, for blood-collection the stroke can be limited to the right volume for the sample needed. Furthermore the finger brace according to the invention is ideal for mass production of prefilled syringes since it can be fitted with ease to the syringe bodies. The stop tube automatically centers the brace while it is pushed on the body and its side portions are deflected outward to allow the teeth to snap into place under the rim of the syringe body.

According to the invention the plate is generally rectangular and the collar has two such teeth and side portions diametrically opposite each other. Each side portion is straight and the collar is formed with a pair of corner portions connecting the side portions to the rest of the collar. The corner portions are arcuate.

The body in accordance with the invention has an inside diameter generally corresponding to an outside diameter of the tube. In addition the tube has a front edge lying axially forward of a front edge of the collar. The rim is oval and a rear face of the plate is formed around the hole with a frustoconical bevel. The end plate, tube, and collar are unitarily formed with one another, normally of a durable plastic.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
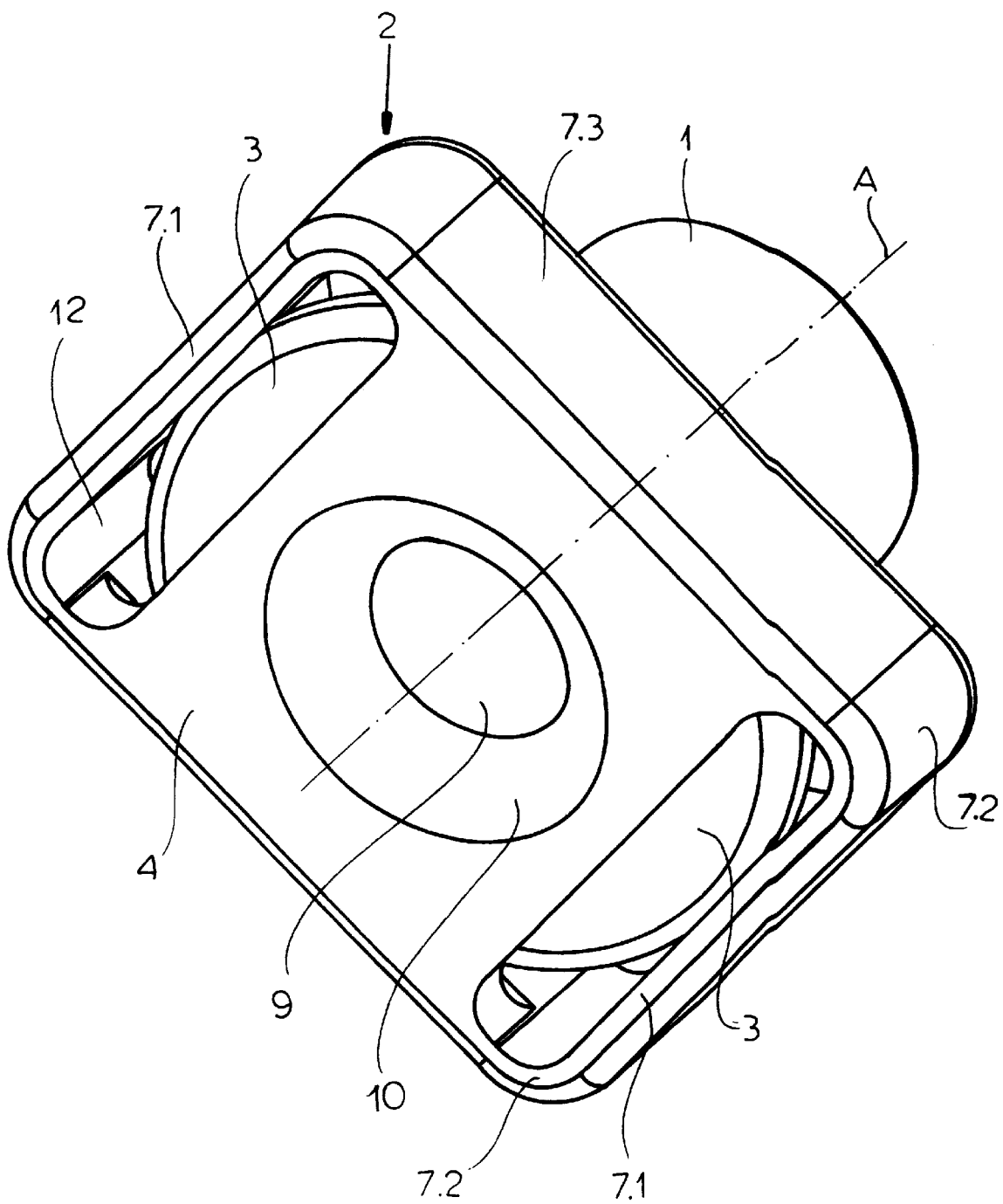
FIG. 1 is a perspective view from the rear of a finger brace and syringe body.
Figure 2:
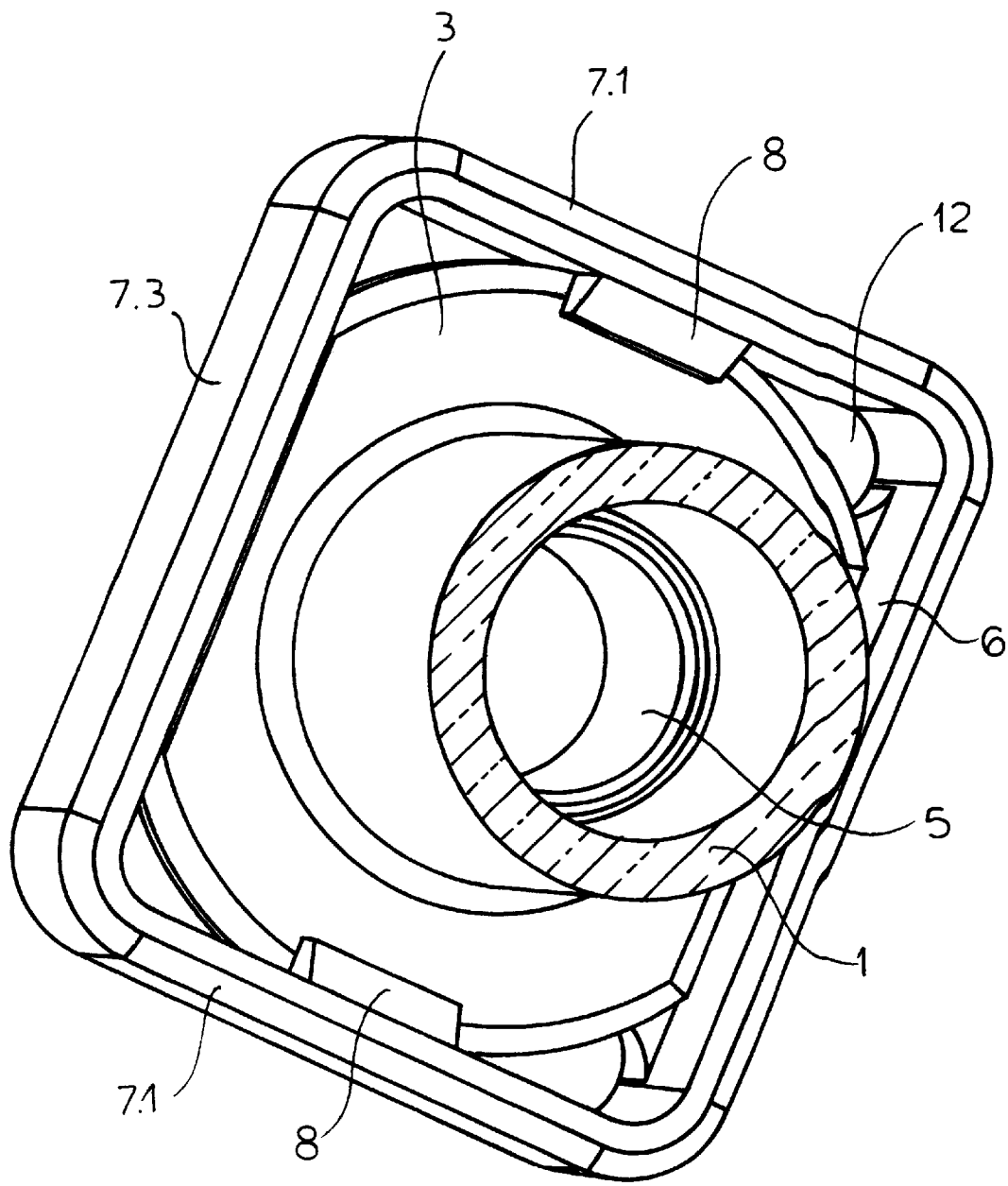
FIG. 2 is a partly sectional perspective view from the front of the structure of FIG. 1.
Figure 3:
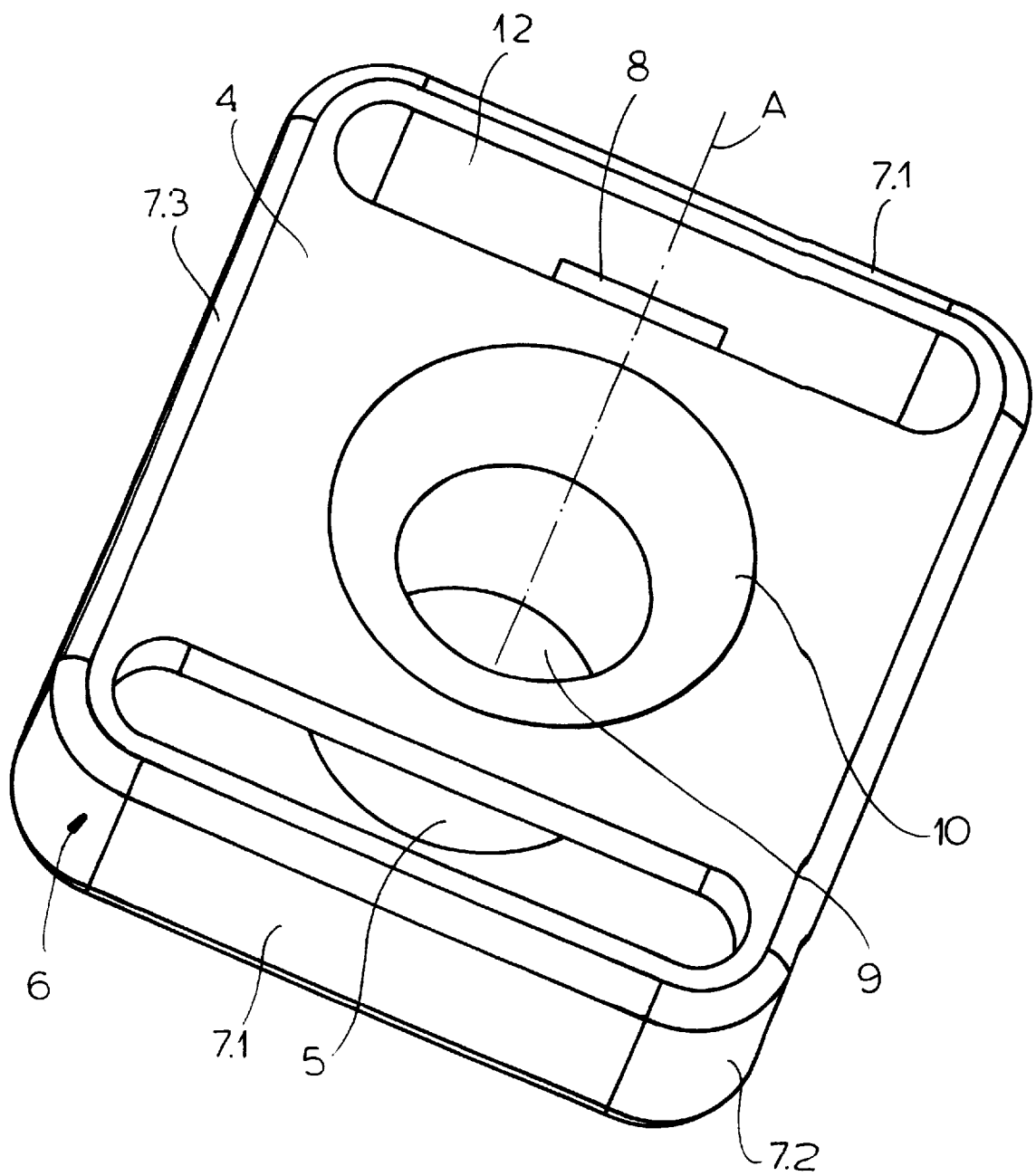
FIGS. 3 and 4 are perspective views respectively from the rear and front of the finger brace all alone.
Figure 4:
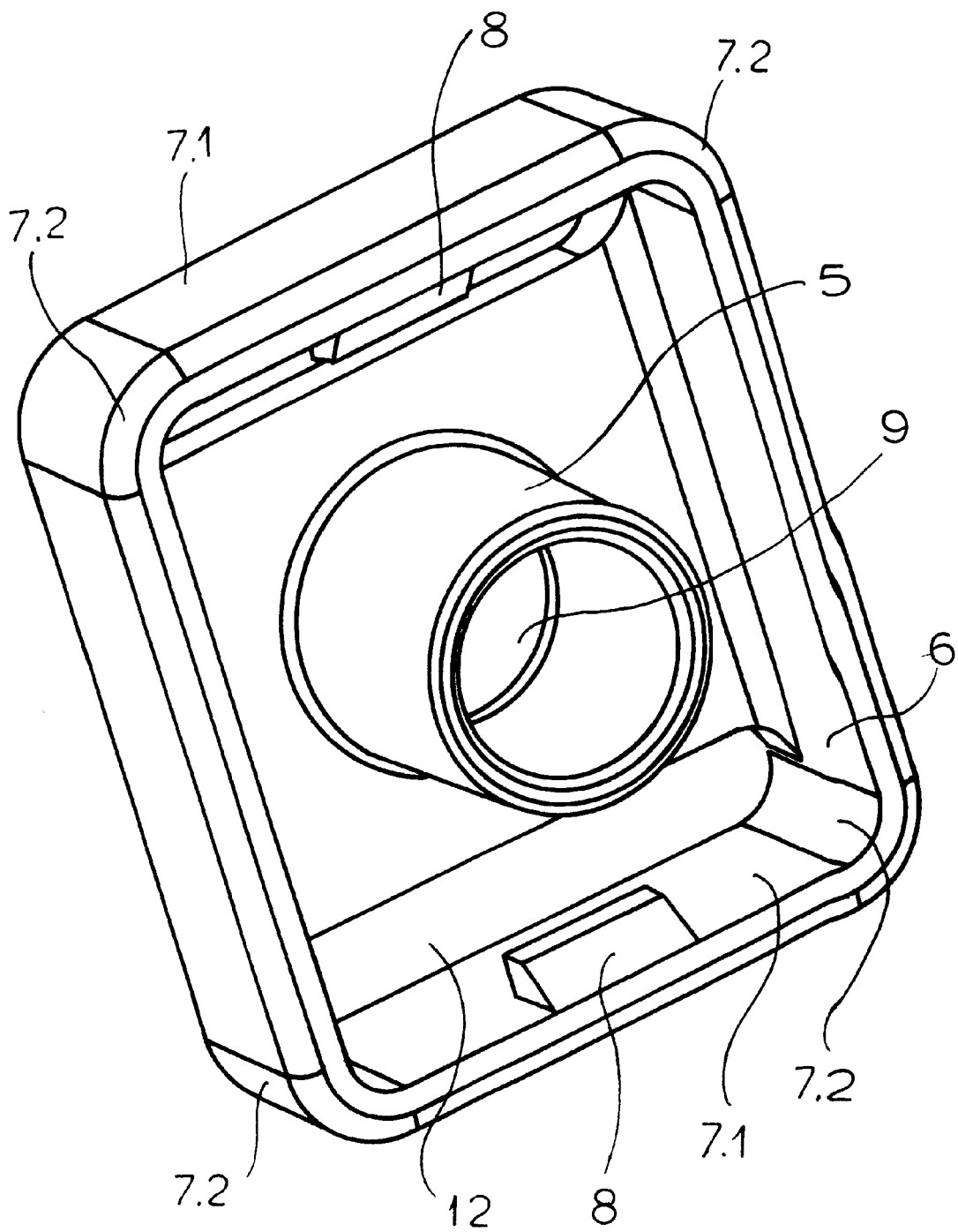

As seen in FIGS. 1 and 2 a syringe has a tubular glass or plastic body (see also FIG. 5d) centered on an axis A and formed at its rear end with an oval and radially outwardly projecting rim 3 adapted to carry a finger brace 2 made of a stiff but elastically deformable plastic. The oval shape of the rim is normally produced by shaping or clipping the sides of an initially circular rim.

The finger brace 2 according to the invention basically comprises a planar and rectangular base plate 4 extending perpendicular to the axis A and formed centered on the axis A with a forwardly projecting tube 5 and with a forwardly projecting basically rectangular collar 6. The tube 5 has an outside diameter slightly smaller than an inside diameter of the syringe body 1 and extends axially forward somewhat past a front edge of the collar 6. The tube 5 defines a cylindrical throughgoing hole 9 and a rear surface of the plate 4 is formed with a frustoconical bevel 10 around this hole 9.

According to the invention the plate 4 is formed along two sides with an elongated throughgoing cutout 12 each forming in the collar 6 a deflectable but normally straight side portion 7.1 and a pair of 90° arcuate corner portions 7.2. The side portions 7.1, which are parallel to each other and diametrically across from each other, each carry a respective inwardly projecting engagement formation or tooth 8 that is spaced forward (toward the needle end of the body 1) from the front face of the plate 4 by a distance equal to the axial thickness of the rim 3 so that they can snap under the rim 3 and secure the brace 2 in place thereon. The other side portions 7.3 of the collar 6 lie against the flatted sides of the generally oval rim 3 so that the finger brace 2 cannot rotate about the axis A on the body 1.

Figure 5A:
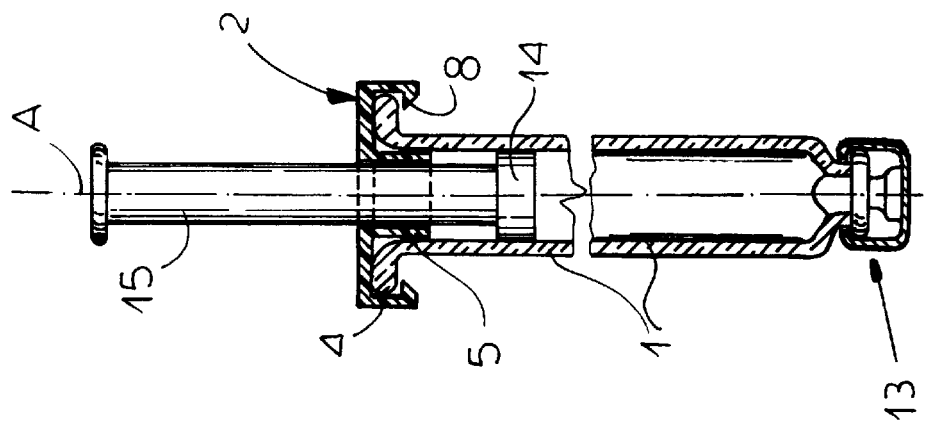
FIGS. 5a through 5d are largely and sectional schematic views illustrating assembly of the syringe according to the invention.
Figure 5B:
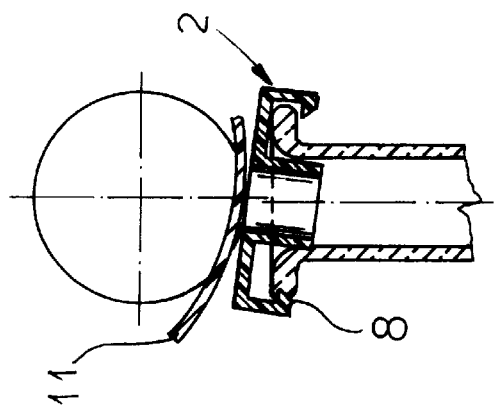
Figure 5C:
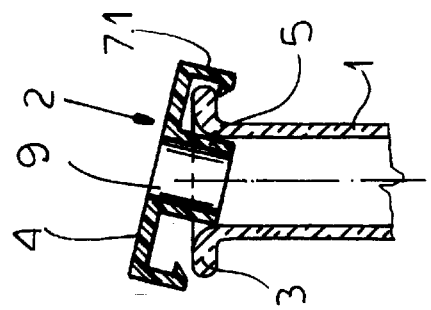
Figure 5D:
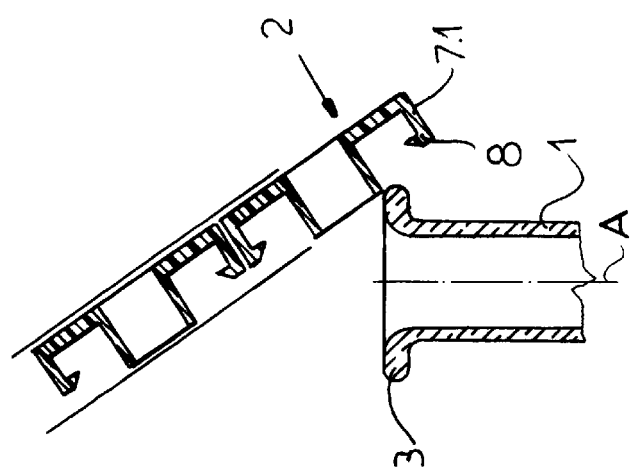

A syringe is assembled in accordance with the invention as shown in FIGS. 5a through 5d by first feeding a finger brace 2 downward at an angle of about 45° to the axis A to the syringe body 1 as shown in FIG. 5a. Then as shown in FIG. 5b one of the teeth 8 is hooked under the rim 3 while the center tube 5, which projects axially forward past the collar 6 as mentioned above, fits into the rear end of the tubular body 1. Then an arcuate tool 11 presses the brace 2 down as shown in FIG. 5c to force the other tooth 8 down over the rim 3, with elastic outward deflection of the respective side portion 7.1 until both teeth 8 are snapped snugly under the rim 3 and the brace 2 is firmly in place as shown in FIG. 5d. An end-cap assembly (see above-mentioned U.S. Pat. No. 5,320,603) is fitted over the front end of the body 1, and a piston 14 with a plunger 15 is fitted through the finger brace 2 to complete the syringe. Then all that is needed is a cannula or needle fitted to the front end for use of the syringe.

According to the invention it is possible to make the tubes 5 of different lengths to limit the rearward travel of the piston 14. This can be useful in a blood-collecting system to ensure that an exact amount of blood is drawn, never too much.

We claim:

1. A syringe assembly comprising:
   a tubular syringe body centered on and extending along an axis and formed at a rear end with a radially outwardly projecting rim; and
   a finger brace of limitedly elastically deformable material and formed unitarily with
      an end plate bearing axially forward on the rear end and formed with a central hole,
      a tube projecting axially forward from the hole of the plate into the body at the rear syringe end, and
      a collar extending axially forward from the plate outside the tube and formed with a plurality of angularly spaced and radially inwardly projecting teeth engaged under the rim, the plate being formed adjacent each of the teeth with an axially throughgoing and angularly elongated slot defining a radially elastically deflectable side portion carrying the respective tooth.

2. The syringe assembly defined in claim 1 wherein the plate is generally rectangular and the collar has two such teeth and side portions diametrically opposite each other.

3. The syringe assembly defined in claim 2 wherein each side portion is straight and the collar is formed with a pair of corner portions connecting the side portions to the rest of the collar.

4. The syringe assembly defined in claim 3 wherein the corner portions are arcuate.

5. The syringe assembly defined in claim 1 wherein the body has an inside diameter generally corresponding to an outside diameter of the tube.

6. The syringe assembly defined in claim 1 wherein the tube has a front edge lying axially forward of a front edge of the collar.

7. The syringe assembly defined in claim 1 wherein the rim is oval.

8. The syringe assembly defined in claim 1 wherein a rear face of the plate is formed around the hole with a frusto-conical bevel.

9. A syringe assembly comprising:
   a tubular and cylindrical syringe body centered on and extending along an axis and formed at a rear end with a radially outwardly projecting rim; and
   a finger brace of limitedly elastically deformable material and formed unitarily with
      a rectangular end plate bearing axially forward on the rear end and formed with a central hole,
      a cylindrical tube projecting axially forward from the hole of the plate into the body at the rear syringe end, and
      a collar extending axially forward from the plate outside the tube and having two opposite sides each formed with a respective radially inwardly projecting tooth engaged under the rim, the plate being formed adjacent each of the teeth with an axially throughgoing and elongated slot defining a radially elastically deflectable and straight side portion carrying the respective tooth.

* * * * *